US008101208B2

(12) United States Patent
Lakkis et al.

(10) Patent No.: US 8,101,208 B2
(45) Date of Patent: *Jan. 24, 2012

(54) SENSATE COMPOSITIONS AND DELIVERY SYSTEMS THEREFOR

(75) Inventors: Jamileh Lakkis, Morris Plains, NJ (US); Susan Pettigrew, Suffern, NY (US)

(73) Assignee: Kraft Foods Global Brands LLC, Northfield, IL (US)

(*) Notice: Subject to any disclaimer, the term of this patent is extended or adjusted under 35 U.S.C. 154(b) by 683 days.

This patent is subject to a terminal disclaimer.

(21) Appl. No.: 11/200,748

(22) Filed: Aug. 10, 2005

(65) Prior Publication Data

US 2006/0034936 A1 Feb. 16, 2006

Related U.S. Application Data

(60) Provisional application No. 60/600,649, filed on Aug. 11, 2004, provisional application No. 60/668,670, filed on Apr. 6, 2005.

(51) Int. Cl.
*A61K 9/50* (2006.01)
*A61K 9/16* (2006.01)
*A61K 47/00* (2006.01)

(52) U.S. Cl. .......................................... 424/490; 424/439

(58) Field of Classification Search .................... 424/439
See application file for complete search history.

(56) References Cited

U.S. PATENT DOCUMENTS

| | | | |
|---|---|---|---|
| 3,485,920 A * | 12/1969 | Bender | 514/164 |
| 3,857,964 A | 12/1974 | Yolles | |
| 3,897,566 A | 7/1975 | Bahoshy et al. | |
| 3,930,026 A | 12/1975 | Clark | |
| 4,032,661 A | 6/1977 | Rowsell et al. | |
| 4,033,994 A | 7/1977 | Watson et al. | |
| 4,059,118 A | 11/1977 | Watson et al. | |
| 4,060,091 A | 11/1977 | Watson et al. | |
| 4,070,449 A | 1/1978 | Rowsell et al. | |
| 4,136,163 A | 1/1979 | Watson et al. | |
| 4,193,936 A | 3/1980 | Watson et al. | |
| 4,230,688 A | 10/1980 | Rowsell et al. | |
| 4,271,197 A | 6/1981 | Hopkins et al. | |
| 4,352,822 A | 10/1982 | Cherukuri et al. | |
| 4,388,328 A | 6/1983 | Glass | |
| 4,459,425 A | 7/1984 | Amano et al. | |
| 4,485,118 A | 11/1984 | Carroll et al. | |

(Continued)

FOREIGN PATENT DOCUMENTS

EP 0 255 260 2/1988

(Continued)

OTHER PUBLICATIONS

International Search Report (mailed Dec. 22, 2005).

(Continued)

*Primary Examiner* — Scott Long
*Assistant Examiner* — Sarah Alawadi
(74) *Attorney, Agent, or Firm* — Cantor Colburn LLP (57) ABSTRACT

The present invention includes compositions for imparting a controlled-release sensation to the oral receptor areas of a user. The oral, controlled-release compositions include a sensate and a hydrated or swollen food-grade polymer which forms a matrix with the sensate. Sensates may include warming, cooling and/or tingling agents. Also included are oral delivery systems for the compositions, methods for preparing same, and methods for imparting and sustaining a desired sensation in the mouth and upper portion of the gastrointestinal tract of the user.

12 Claims, 7 Drawing Sheets

U.S. PATENT DOCUMENTS

| | | | |
|---|---|---|---|
| 4,497,832 A | 2/1985 | Cherukuri et al. | |
| 4,568,560 A | 2/1986 | Schobel | |
| 4,590,075 A | 5/1986 | Wei et al. | |
| 4,722,845 A | 2/1988 | Cherukuri et al. | |
| 4,747,881 A * | 5/1988 | Shaw et al. | 106/172.1 |
| 4,751,095 A | 6/1988 | Karl et al. | |
| 4,752,481 A | 6/1988 | Dokuzovic | |
| 4,803,082 A | 2/1989 | Cherukuri et al. | |
| 4,918,182 A | 4/1990 | Jackson et al. | |
| 4,927,646 A | 5/1990 | Jenner et al. | |
| 4,929,447 A | 5/1990 | Yang | |
| 4,933,190 A | 6/1990 | Cherukuri et al. | |
| 4,971,797 A | 11/1990 | Cherukuri et al. | |
| 4,981,698 A | 1/1991 | Cherukuri et al. | |
| 5,004,595 A | 4/1991 | Cherukuri et al. | |
| 5,009,893 A | 4/1991 | Cherukuri et al. | |
| 5,009,900 A | 4/1991 | Levine et al. | |
| 5,041,294 A | 8/1991 | Patel | |
| 5,158,790 A | 10/1992 | Witkewitz et al. | |
| 5,215,756 A | 6/1993 | Gole et al. | |
| 5,244,670 A | 9/1993 | Upson et al. | |
| 5,266,335 A | 11/1993 | Cherukuri et al. | |
| 5,266,592 A | 11/1993 | Grub et al. | |
| 5,284,659 A | 2/1994 | Cherukuri et al. | |
| 5,372,824 A | 12/1994 | Record et al. | |
| 5,405,604 A | 4/1995 | Hall | |
| 5,407,665 A | 4/1995 | McLaughlin et al. | |
| 5,415,880 A | 5/1995 | Song et al. | |
| 5,429,827 A | 7/1995 | Song et al. | |
| 5,458,879 A | 10/1995 | Singh et al. | |
| 5,545,424 A | 8/1996 | Nakatsu et al. | |
| 5,603,971 A | 2/1997 | Porzio et al. | |
| 5,633,027 A | 5/1997 | Cherukuri et al. | |
| 5,725,865 A | 3/1998 | Mane et al. | |
| 5,744,180 A | 4/1998 | Cherukuri et al. | |
| 5,783,725 A | 7/1998 | Kuhn et al. | |
| 5,800,848 A | 9/1998 | Yatka et al. | |
| 6,159,509 A | 12/2000 | Johnson et al. | |
| 6,258,341 B1 * | 7/2001 | Foster et al. | 424/45 |
| 6,306,429 B1 | 10/2001 | Bealin-Kelly | |
| 6,365,209 B2 * | 4/2002 | Cherukuri | 426/72 |
| 6,379,652 B1 | 4/2002 | Liu et al. | |
| 6,432,441 B1 | 8/2002 | Bealin-Kelly et al. | |
| 6,623,266 B2 | 9/2003 | Jani et al. | |
| 6,627,233 B1 | 9/2003 | Wolf et al. | |
| 6,673,844 B2 | 1/2004 | Kumamoto et al. | |
| 6,780,443 B1 | 8/2004 | Nakatsu et al. | |
| 6,838,106 B2 | 1/2005 | Kumamoto et al. | |
| 6,899,901 B2 * | 5/2005 | Nakatsu et al. | 424/725 |
| 7,189,760 B2 | 3/2007 | Erman et al. | |
| 7,488,503 B1 * | 2/2009 | Porzio et al. | 426/293 |
| 2002/0044968 A1 | 4/2002 | Van Lengerich | |
| 2002/0119231 A1 | 8/2002 | Kumamoto et al. | |
| 2002/0150616 A1 | 10/2002 | Vandecruys | |
| 2003/0215532 A1 | 11/2003 | Nakatsu et al. | |
| 2004/0238993 A1 | 12/2004 | Benczedi et al. | |
| 2005/0019445 A1 | 1/2005 | Wolf et al. | |
| 2005/0196517 A1 | 9/2005 | Hodanko et al. | |
| 2006/0035008 A1 * | 2/2006 | Virgallito et al. | 426/650 |
| 2007/0036733 A1 | 2/2007 | Spence et al. | |
| 2007/0048424 A1 | 3/2007 | Moza et al. | |

FOREIGN PATENT DOCUMENTS

| | | |
|---|---|---|
| EP | 0 434 321 | 6/1991 |
| EP | 0 452 273 | 10/1991 |
| EP | 0 453 397 | 10/1991 |
| EP | 1 121 927 | 8/2001 |
| EP | 1 215 258 A2 | 6/2002 |
| EP | 0 888 067 B1 | 12/2003 |
| EP | 1 003 475 B1 | 1/2004 |
| GB | 1351761 | 5/1974 |
| JP | 01-206969 | 8/1989 |
| WO | WO 85/03414 | 8/1985 |
| WO | WO 90/04926 | 5/1990 |
| WO | WO 92/02145 | 2/1992 |
| WO | WO 93/23005 | 11/1993 |
| WO | WO 93/25177 | 12/1993 |
| WO | WO/95/07683 | 3/1995 |
| WO | WO 95/11671 | 5/1995 |
| WO | WO 96/03109 | 2/1996 |
| WO | WO 96/17524 | 6/1996 |
| WO | WO/97/02273 | 1/1997 |
| WO | WO 97/06695 | 2/1997 |
| WO | WO 97/24036 | 7/1997 |
| WO | WO 98/03076 | 1/1998 |
| WO | WO/98/47483 | 10/1998 |
| WO | WO 98/47484 | 10/1998 |
| WO | WO 98/52540 | 11/1998 |
| WO | WO/98/52545 | 11/1998 |
| WO | 9913734 A1 | 3/1999 |
| WO | WO 99/13870 | 3/1999 |
| WO | WO 02/00039 | 1/2002 |
| WO | WO/02/76211 * | 3/2002 |
| WO | WO 03/063604 | 8/2003 |
| WO | 03088755 A1 | 10/2003 |
| WO | WO/03/106404 A1 | 12/2003 |
| WO | WO 2004/006967 | 1/2004 |
| WO | WO/2004/064544 | 8/2004 |
| WO | 2005/082154 | 9/2005 |
| WO | 2006/003349 | 1/2006 |
| WO | WO 2006/039945 | 4/2006 |

OTHER PUBLICATIONS

Anonymous; "Caprol 3GO CAS No. 9007-48-1" XP002401201. Retrieved from the Internet: URL: http://www.abiteccorp.com/documents/3go-17_000.pdf> [retrieved on Sep. 28, 2006].

Anonymous; "HLB Systems" [Online] pp. 1-4, XP002401202. Retrieved from the Internet: URL: http://pharmcal.tripod.com/ch17.htm. [retrieved on Sep. 28, 2006].

*Quantitative Model Studies on the Efficiency of Precursors in the Formation of Cooling-Active 1-Pyrrolidinyl-2-cyclopenten-1-ones and Bitter-Tasting Cyclopenta-[b]azepin-8(1H)-ones*; Journal of Agricultural and Food Chemistry; 2002; pp. 5156-5161.

Leffingwell, John C. "Cool without Menthol & Cooler than Menthol and Cooling Compounds as Insect Repellents." From the Internet: URL: http://www.leffingwell.com/cooler_than_menthol.htm [updated Apr. 5, 2006].

JP 04-293454; Oct. 19, 1992; Abstract Only (1 page).

U.S. Appl. No. 11/201,370 Restriction Requirement dated: Apr. 9, 2008, 12 pages.

U.S. Appl. No. 11/201,370 Non-Final Office Action dated: Jun. 9, 2008, 9 pages.

U.S. Appl. No. 11/201,370 Final Office Action dated: Nov. 18, 2008, 10 pages.

U.S. Appl. No. 11/201,370 Final Office Action dated: Apr. 29, 2010, 10 pages.

U.S. Appl. No. 11/201,370 Final Office Action dated: May 17, 2010, 10 pages.

U.S. Appl. No. 11/201,370 Non-Final Office Action dated: Sep. 13, 2010, 10 pages.

* cited by examiner

FIG. 7

SENSATE COMPOSITIONS AND DELIVERY SYSTEMS THEREFOR

CROSS-REFERENCE TO RELATED APPLICATIONS

This application claims the benefit of U.S. Provisional Application No. 60/600,649, filed Aug. 11, 2004 and U.S. Provisional Application No. 60/668,670, filed Apr. 6, 2005, the contents all of which are incorporated herein by reference.

FIELD

The present invention includes compositions for imparting a controlled-release sensation to the oral receptor areas of a user, i.e., a mammal. In particular, the oral, controlled-release compositions of the present invention include a sensate and a hydrated or swollen food-grade polymer which forms a matrix with the sensate. The present invention also relates to oral delivery systems and methods for preparing same, as well as methods for imparting and sustaining a desired sensation in the mouth, throat and upper portion of the gastrointestinal tract of a user.

BACKGROUND

A variety of compounds which provide a sensation of warmth on application are known, and are commonly referred to as "warming agents." Compounds which provide a cooling sensation also are known and commonly referred to as "cooling agents" or "physiological cooling agents." Warming and/or cooling agents are added to a variety of manufactured products, including both topical and ingestible products, to produce a warming and/or cooling effect, which is pleasing to the user.

Compounds which provide a tingling sensation also are known and referred to as "tingling agents." Tingling agents also may be added to a variety of manufactured products, both topical and ingestible, to provide a tingling, stinging or numbing sensation, as desired.

When incorporated into ingestible products, however, such warming, cooling and tingling agents typically exhibit insufficient effects. In particular, although conventional ingestible products may provide a sensation in the mouth of the user, this sensation is perceived only briefly and most often never reaches the receptors in the throat. In order to extend the sensation into the throat area, higher concentrations of the compounds may be required. This approach often results in undesirable stinging or burning sensation in the mouth.

There is a need, therefore, for new oral compositions, which incorporate warming, cooling and/or tingling agents and provide the desired sensation not only in the mouth but also in the throat and upper portion of the gastrointestinal tract of the user. There is also a need for oral compositions that extend the length of time that the desired sensation is perceived by the user. Further, there is a need for delivery systems for such oral compositions and methods of preparing same.

SUMMARY

In some embodiments there is an oral composition, which includes: a sensate; and a hydrated food-grade polymer which forms a non-particulate matrix with the sensate.

In some embodiments there is an oral composition, including: a sensate; and a swollen food-grade polymer which forms a non-particulate matrix with the sensate.

In some embodiments, an oral, controlled-release composition includes: a sensate; a food-grade polymer which forms a non-particulate matrix with the sensate; and a carrier selected from a wet carrier and a swelling agent.

In some embodiments, an oral, controlled-release composition includes: a sensate; and a saccharide which forms a non-particulate matrix with the sensate.

In some embodiments, there is an oral composition including: a homogenous matrix comprising a blend of a hydrated food-grade polymer and at least one sensate.

In some embodiments, an oral composition includes: a sensate dispersed in a hydrated food-grade polymer.

In some embodiments, an oral composition includes: a senate dispersed in a hydrated food-grade polymer blend, which includes a hydrophilic polymer and a hydrophobic polymer.

In some embodiments there is an oral composition which includes: a sensate dispersed in a hydrated food grade polymer that increases the viscosity of the saliva of a mammal.

In some embodiments there is a comestible including: an oral composition including a sensate and a hydrated food-grade polymer which forms a non-particulate matrix with the sensate; a flavor agent; and a carrier.

In some embodiments there is a lozenge composition including: a glassy polymer matrix having a sensate dispersed therein.

In some embodiments there is a chewing gum composition including: an oral composition which includes a sensate and a hydrated food-grade polymer which forms a non-particulate matrix with the sensate; a flavor agent; and a gum base, wherein the food-grade polymer is present in an amount sufficient to produce a sensation in the mouth and upper gastrointestinal tract of a mammal extending from about 2 seconds to about 1 hour.

In some embodiments there is a method of preparing a comestible which imparts a controlled release sensation to the mouth and throat of a mammal, which includes the steps of: heating a carrier with an aqueous solution of a food-grade polymer until the carrier changes from a crystalline phase to an amorphous or a glassy phase; dispersing a sensate in the polymer to form a non-particulate matrix; and forming a comestible from the combination of components in the glassy phase.

In some embodiments, a method of imparting a sensation to oral receptor areas of a mammal includes the steps of: orally administering a composition containing a sensate and a hydrated food-grade polymer which forms a non-particulate matrix with the sensate; and stimulating the oral receptor areas within about 2 to about 45 seconds to produce a sensation in the mouth and upper gastrointestinal tract of the mammal.

In some embodiments, a method of sustaining a sensation in the mouth and upper gastrointestinal tract of a mammal includes the steps of: orally administering a comestible containing a sensate and a hydrated food-grade polymer which forms a non-particulate matrix with the sensate; and stimulating oral receptor areas of the mammal to produce a sensation in the mouth and upper gastrointestinal tract, wherein the polymer is present in an amount sufficient to produce a sensation in the mouth and upper gastrointestinal tract extending from about 2 seconds to about 30 minutes.

DETAILED DESCRIPTION

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum" and "chewing gum" are used interchangeably and are both meant to include any gum compositions.

The term "food-grade polymer," as used herein, encompasses any polymer that is acceptable for use in edible compositions.

Sensate Compositions

Embodiments described herein provide an oral, controlled release composition that stimulates the oropharyngeal receptor areas of a user. The compositions thereby impart a sensation to the mouth, throat and upper gastrointestinal tract of the user. The compositions include a sensate, such as a warming, cooling and/or tingling agent, and a hydrated or swollen food-grade polymer which forms a matrix with the sensate.

The term "matrix" refers to a medium whereby the sensate and the food-grade polymer are dispersed allowing potential chemical and/or physical interactions between these two components. For instance, polymers, such as, but not limited to, pectin, interact with sensates, both chemically and/or physically to permit sustained, or controlled, release of the sensate from the composition. The matrix may be non-particulate, such that the sensate is dispersed in the polymer, in contrast to encapsulation of particulate spheres of a sensate. For example, in some embodiments the sensate may be embedded in the polymer. The dispersion of the sensate in the polymer may be homogenous, or uniform, or it may be a non-uniform dispersion of components.

With respect to some embodiments, the matrix may be described as a "glassy candy matrix," or "glassy matrix." Such terms interchangeably refer to the glassy phase of components used to prepare a lozenge or similar hard candy product of the present invention. The glassy matrix is a dispersion of the sensate in the food-grade polymer and a carrier used to make the manufactured product.

The food-grade polymer and sensate matrix provides for a sustained, or controlled release of the sensate from the oral composition. This extends the sensation in both time and location. In particular, the sensate is released at a slower rate than conventional sensates, thereby extending the length of sensation perceived by the user. The sensate also reaches a greater amount of oral receptor areas innervated by the trigeminal nerves. The polymer matrix enables the sensate to reach receptors in not only the mouth but also the throat of the user. Stimulation of these oropharyngeal receptor areas provides a sensation in both the mouth and upper portion of the gastrointestinal tract, a result of the innervation of the pharynx and perhaps the larynx branches of the glossopharyngeal and vagus nerves. Some individuals may even perceive the sensation down to their stomach, presumably due to high permeability of the mucosa and possible differences in the spatial distribution of the fibers they stimulate.

The food-grade polymer, which interacts with the sensate to provide control of release into the oral cavity, may be any conventional polymer used in edible compositions, which is hydrated or swollen. In some embodiments of the present invention, a carrier is included, which may be a wet carrier or a swelling agent. Wet carriers desirably provide a sufficient amount of moisture or liquid to hydrate and/or dissolve the food-grade polymer. Swelling agents desirably provide a sufficient amount of moisture or liquid to swell the food-grade polymer. For example, for simple sugars, such as glucose and sucrose, the wet carrier or swelling agent is present in amounts of about 5% to about 95% by weight of the hydrated or swollen food-grade polymer component. For large polymers, such as pectins and carboxymethyl cellulose, the wet carrier or swelling agent is present in amounts of about 20% to about 99.9% by weight of the hydrated or swollen food-grade polymer component. For pectins, as well as other hydrocolloids and polysaccharides, for example, the wet carrier may be water present in amounts of about 85% to about 99.5% by weight of the hydrated food-grade polymer component. Suitable wet carriers or swelling agents include, but are not limited to, water, organic solvents and plasticizers, such as, for example, low melting fats. Desirably, the wet carrier hydrates the polymer to form a gel or like semi-solid consistency.

General categories of suitable polymers include, for example, saccharides, proteins, glycoproteins, oligoproteins, fats and waxes. Combinations of polymers also may be employed.

Saccharides include di-saccharides, oligo-saccharides and polysaccharides. Mono-saccharides, though not polymers, may even be used in some embodiments. Suitable examples of saccharides include, but are not limited to: ribose; mannose; galactose; polydextrose; corn syrup; dextrins; honey; carob powder; molasses; date sugar; rice syrup; agave syrup; fructo-oligosaccharides, such as insulin; starches, both modified and natural, and starch fractions including amylose and amylopectin; pectins, such as low and high molecular weight methoxy pectins; alginates, such as sodium and potassium; natural and synthetic gums, such as gum arabic, gellan gum, welan gum, gum tragacanth, xanthan gum, guar gum, and locust bean gum; celluloses, such as carboxymethyl cellulose, hydroxypropyl cellulose, hydroxymethyl cellulose, hydroxybutyl carboxymethyl cellulose, hydroxypropylethyl cellulose and methylethyl cellulose; carrageenans, such as alpha-, gamma-, iota-, kappa- and lambda carrageenans; and combinations thereof.

Useful proteins may be selected from a wide variety of materials. Suitable proteins include, for example: gelatin; caseins and caseinates; whey proteins; soy proteins; wheat proteins; corn proteins; barley proteins; egg proteins; muscle proteins; proteins from other legumes and tubers; and combinations thereof. Glycoproteins include, for example, chondroitins, glucosaminoglycans and lectins. Glycolipids also may be employed.

Fats include both saturated and unsaturated fats. Waxes include, for example, bees wax, carnauba wax, low melting paraffins, shellac, candelilla wax, microcrystalline and synthetic waxes.

Some embodiments of the present invention employ polyvinyl pyrrolidone, polyvinyl alcohol, anionic polymer of methacrylic acid and methacrylate, polyvinyl acetate, polyethylene oxide and/or polyethylene as the food-grade polymer.

Combinations of food-grade polymers also may be employed in some embodiments. For example, blends of a hydrophilic polymer and a hydrophobic polymer may be employed. Hydrophilic polymers allow for a rapid impact of the sensation in the oral cavity, while hydrophobic polymers may provide a more delayed impact but may also provide a longer lasting sensation. Combinations of the two polymers, therefore, may be employed to balance these properties, i.e., achieve rapid impact as well as sustained sensation. Suitable combinations include, for example, hydrophilic proteins with hydrophobic waxes.

Polymer viscosity and molecular weight also may affect the impact of the sensation. In general, the viscosity of the food-grade polymer ranges from about 2 cP to about 100,000 cP. For example, the viscosity of pullulan is about 2 cP, the viscosity of carboxymethyl cellulose can reach as high as 20,000 cP, the viscosity of xanthan gum ranges from about 10 cP to about 100,000 cP, and the viscosities of pectin and welan gum can be as high as thousands cP. Polymer viscosity varies with a number of properties, such as, concentration in solution, shear rate to which the polymer solution is subjected as well as its behavior under shear (Newtonian, non-Newtonian, viscoelastic, etc.), temperature and presence of ions, among others. Lower viscosity polymers generally provide relatively shorter impact of the sensation, whereas polymers having higher viscosities provide relatively longer lasting impact. In accordance therewith, some embodiments of the present invention combine low and high viscosity polymers to balance the properties of the sensate composition, including the impact and duration of the sensation.

Certain food grade polymers, particularly those described above, can increase the viscosity of the saliva, thereby increasing the sensate's residence time in the oropharyngeal area, in particular in the throat. In accordance therewith, some embodiments of the present invention incorporate food grade polymers that increase the viscosity of saliva. Particularly suitable polymers include pectins, alginates, fructo-oligosaccharides, proteins and the like.

Molecular weight of the food-grade polymer may range anywhere from about 180 up to several million Daltons for high-molecular weight polymers. Molecular weight of pullulan, for example, ranges from 95,000 up to 124,000 (for pullulan P100 and pullulan P1200, respectively). Pectins' molecular weights range from 90,000 Daltons for citrus pectins up to 135,000 Daltons for red tomato pectins, or even higher. Proteins' molecular weights can range from few hundreds (simple peptides) up to million Daltons (e.g., myosin). High molecular weight polymers, particularly pectin, generally provide slower release of the sensate into the oral cavity.

Glass transition temperature is another property that affects the release of the sensate. The hydrated food-grade polymers used in embodiments of the present invention generally have a glass transition temperature of about −50° C. to about 80° C.

The food-grade polymer may be present in the sensate composition in amounts sufficient to extend the sensation in the mouth, throat and upper gastrointestinal tract from about two seconds to about thirty minutes. In some embodiments, the warming sensation may be almost immediate. In some embodiments, the warming sensation is perceived from less than about one minute to about ten minutes. More specifically, oral receptor areas are stimulated by the release of the sensate within about two to forty-five seconds, more specifically, about thirty to forty-five seconds. Within less than one minute, therefore, a sensation is felt in the mouth and upper gastrointestinal area, which extends for about thirty minutes. The sensation may be sustained for about one to three minutes, or even longer in some embodiments, after the composition is substantially consumed without imparting a burning sensation. In accordance therewith, the polymer is present in amounts of about 0.05% to about 99% by weight of the sensate composition. In some embodiments, the polymer is present in amounts of about 1% to about 10% by weight of the composition.

The sensate may be a warming, cooling or tingling agent or any combination thereof.

Warming agents may be selected from a wide variety of compounds known to provide the sensory signal of warming to the individual user. These compounds offer the perceived sensation of warmth, particularly in the oral cavity, and often enhance the perception of flavors, sweeteners and other organoleptic components. Useful warming agents include those having at least one allyl vinyl component, which may bind to oral receptors. Examples of suitable warming agents include, but are not limited to: vanillyl alcohol n-butylether (TK-1000, supplied by Takasago Perfumery Company Ltd., Tokyo, Japan); vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof.

A variety of well-known cooling agents may be employed in the oral compositions. For example, among the useful cooling agents are included menthol, xylitol, erythritol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol and glutarate esters, among others, and combinations thereof. These and other suitable cooling agents are further described in the following U.S. patents, all of which are incorporated in their entirety by reference hereto: U.S. Pat. Nos. 4,230,688 and 4,032,661 to Rowsell et al.; U.S. Pat. No. 4,459,425 to Amano et al.; U.S. Pat. No. 4,136,163 to Watson et al.; and U.S. Pat. No. 5,266,592 to Grub et al. Physiological cooling agents also may enhance the sensation of warmth perceived by the user, and therefore, combinations of warming and cooling agents may be employed in some embodiments.

Tingling agents may be employed in the oral compositions to provide a tingling, stinging or numbing sensation to the user. Tingling agents include, but are not limited to: Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; black pepper extract (piper nigrum), including the active ingredients chavicine and piperine; Echinacea extract; Northern Prickly Ash extract; red pepper oleoresin; and effervescing agents, such as edible acids and bases, which may be encapsulated. Tingling agents are described in U.S. Pat. No. 6,780,443 to Nakatsu et al., U.S. Pat. No. 5,407,665 to McLaughlin et al., U.S. Pat. No. 6,159,509 to Johnson et al. and U.S. Pat. No. 5,545,424 to Nakatsu et al., each of which is incorporated by reference herein in its entirety.

Edible acids and bases for use as effervescing agents may be encapsulated as microcapsules or microparticles as described in PCT Publication No. WO 2004/064544, which is incorporated herein by reference in its entirety. Suitable encapsulants include, but are not limited to, fats, polymers, carbohydrates and combinations thereof. Suitable bases include, but are not limited to, alkali metal carbonates, alkali metal bicarbonates, alkaline earth metal carbonates, alkaline earth metal bicarbonates and combinations thereof. Suitable acids include, but are not limited to, citric acid, phosphoric acid, tartaric acid, malic acid, ascorbic acid or combinations thereof.

The sensate generally may be present in amounts of about 0.1% to about 96% by weight of the oral composition. In some embodiments, the sensate is present in amounts of about 5% to about 25% by weight of the composition.

In some embodiments of the present invention, the sensate may be dispersed in pectin to form the non-particulate matrix. In such embodiments, pectin may be present in amounts of about 0.05% to about 99% by weight, more desirably about 0.05% to about 10% by weight. The sensate may be present in amounts of about 0.005% to about 96% by weight, more desirably about 0.005% to about 10% by weight.

In some particular embodiments, the oral composition may include a sensate present in amounts of about 0.1% to about 99.9% by weight of the composition and a hydrated pectin matrix present in amounts of about 0.1% to about 99.9% by weight of the composition.

In some embodiments, the oral composition may include a mixture of a sensate and carrier (alcohol, oil and/or aqueous solvents) present in amounts of about 0.1% to about 99.9% by weight of the composition and a hydrated food-grade polymer present in amounts of about 0.1% to about 99.9% by weight of the composition.

In some embodiments, the oral composition may include optional additives such as flavor agents (flavors, flavorings), sweetening agents (sweeteners), coloring agents (colorants, colorings), enhancement components, and the like, and mixtures thereof.

Enhancement components may be added to enhance the perception of warmth, coolness or tingling to the user. The addition of enhancement components allows the sensate to be present at lower levels without compromising the intensity of the desired sensation. Such components include, for example, ionic enhancement components. Ionic enhancement components include mineral cations, such as, magnesium, sodium, calcium, potassium, aluminum; phosphorous and combinations thereof. The ionic enhancement component functions by changing the ionic concentration of the user's saliva and subsequently enhancing diffusion through the mucosal membranes. Because oral receptors are highly ion sensitive, the message of warmth, coolness or tingling is delivered to the brain more rapidly than in the absence of such ionic components.

Delivery Systems

Some embodiments of the present invention provide delivery systems for the oral sensate compositions described above. The delivery systems (also referred to as "comestibles") generally encompass any edible or consumable compositions, such as foods and beverages. More particularly, the comestible may be selected from forms such as, but not limited to, hard candy, soft candy, cotton candy, pressed tablets, chewing gum, film, lozenges, center-filled confectioneries, such as gel or liquid filled confectioneries in any shape, liquid beverages, powdered beverages, and the like. Such comestibles include an oral sensate composition, a flavor agent and a carrier.

As described in detail above, the oral composition includes a sensate and a hydrated or swollen food-grade polymer which forms a matrix therewith. The food-grade polymer may be selected from those described above. In general, the food-grade polymer is present in amounts of about 0.01% up to 98% by weight of the comestible. In some embodiments, the polymer is present in amounts of about 0.2% to about 0.4% by weight. It may be desirable to vary the amount of polymer depending on the comestible form being prepared.

As described above, the glass transition temperature of the hydrated food-grade polymer ranges from about −50° C. to about 80° C.

The oral composition also includes a sensate, as described above. The sensate generally is present in amounts of about 0.001% to about 10% by weight of the comestible. In some embodiments, the sensate is present in amounts of about 0.4% to about 0.6% by weight. Depending upon the type of comestible being prepared, it may be desirable to vary the amount of sensate incorporated therein as certain forms are consumed more rapidly than others.

The carrier component may be selected from a variety of well-known carriers in the art. Selection of suitable carriers depends upon the type of comestible being prepared.

For example, some embodiments are directed to a comestible in the form of a lozenge or candy, also commonly referred to as confectioneries. The carrier in confectionery compositions may include bulk sweeteners such as sugars, sugarless bulk sweeteners, or the like, or mixtures thereof. Bulk sweeteners generally are present in amounts of about 0.05% to about 99% by weight of the composition.

Suitable sugar sweeteners generally include mono-saccharides, di-saccharides and poly-saccharides such as but not limited to, sucrose (sugar), dextrose, maltose, dextrin, xylose, ribose, glucose, mannose, galactose, fructose (levulose), invert sugar, fructo oligo saccharide syrups, partially hydrolyzed starch, corn syrup solids and mixtures thereof.

Suitable sugarless bulk sweeteners include sugar alcohols (or polyols) such as, but not limited to, sorbitol, xylitol, mannitol, galactitol, maltitol, hydrogenated isomaltulose (ISOMALT), lactitol, erythrytol, hydrogenated starch hydrolysate, stevia and mixtures thereof.

Suitable hydrogenated starch hydrolysates include those disclosed in U.S. Pat. Nos. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

In some embodiments, high-intensity sweeteners also may be included in the confectionery compositions. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), N-[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose; 1',6'-dichloro 1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro4,6,1',6'-tetradeoxygalacto-sucrose; and 4,6,1',6'-tetradeoxy-sucrose, and mixtures thereof;

(e) protein based sweeteners such as thaumaoccous danielli (Thaumatin I and II); and (f) the naturally occurring sweetener monatin (2-hydroxy-2-(indol-3-ylmethyl)-4-aminoglutaric acid) and its derivatives.

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

In general, an effective amount of intense sweetener may be utilized to provide the level of sweetness desired, and this amount may vary with the sweetener selected. The intense sweetener may be present in amounts from about 0.001% to about 3%, by weight of the lozenge or candy composition, depending upon the sweetener or combination of sweeteners used. The exact range of amounts for each type of sweetener may be selected by those skilled in the art.

The confectionery composition also includes a flavor agent. Flavor agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof.

In some embodiments, the flavor agent may be employed in either liquid form and/or dried form. When employed in the latter form, suitable drying means such as spray drying the oil may be used. Alternatively, the flavor agent may be absorbed onto water soluble materials, such as cellulose, starch, sugar, maltodextrin, gum arabic and so forth or may be encapsulated. The actual techniques for preparing such dried forms are well-known.

In some embodiments, the flavor agents may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

The amount of flavor agent employed herein may be a matter of preference subject to such factors as the type of final comestible, such as a lozenge, candy composition or chewing gum composition; the individual flavor; the carrier employed; and the strength of flavor desired. Thus, the amount of flavoring may be varied in order to obtain the result desired in the final product and such variations are within the capabilities of those skilled in the art without the need for undue experimentation. In lozenge or candy compositions, the flavor agent is generally present in amounts from about 0.02% to about 5%, and more specifically from about 0.1% to about 2%, and even more specifically, from about 0.8% to about 1.8%, by weight of the composition.

A variety of traditional ingredients also may be included in the confectionery compositions in effective amounts such as coloring agents, antioxidants, preservatives, and the like. Coloring agents may be used in amounts effective to produce the desired color. The coloring agents may include pigments which may be incorporated in amounts up to about 6%, by weight of the composition. For example, titanium dioxide may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfonium-benzylamino) diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Other conventional additives known to one having ordinary skill in the art also may be used in the confectionery compositions.

Enhancement components, as described above, also may be included in the confectionery compositions. Addition of an enhancement component, such as an ionic enhancer, allows for lower levels of sensates to be included in the compositions without compromising the intensity of the desired sensation. For example, some confectionery embodiments include about 0.01% to about 1% sensate by weight, accompanied by an enhancement component.

In some embodiments, and particularly in confectionery compositions, the food-grade polymer employed is desirably pectin. Pectins are water-soluble polysaccharides conventionally used in a variety of food products as gelling agents. It has been discovered that high molecular weight pectins, for example about 9,000 Daltons to about 160,000 Daltons, are highly effective in sustaining the release of sensates in the oral cavity.

Accordingly, pectin may be incorporated in the confectionery composition in amounts sufficient to extend the release of the sensate such that a sensation is perceived by the user within about two seconds to about thirty minutes. In general, a lozenge or candy is substantially consumed by the user within about fifteen minutes. Lozenges and candies, however, may be adapted to be small or larger to alter consumption times. During consumption, the user perceives the desired sensation in the mouth, throat and upper gastrointestinal tract within about 2-45 seconds. The user may continue to perceive this sensation for up to about four minutes, or even longer, e.g., up to about fifteen minutes, after the confectionery is substantially consumed, i.e., aftertaste sensation.

To achieve such controlled release of the sensate, pectin may be incorporated into some confectionery embodiments in amounts of about 0.2% to about 0.4% by weight. Using amounts of pectin less than about 0.2% by weight, e.g. about 0.1%, or greater than about 0.4% by weight, also may have the effect of sustaining release of the sensate, however such amounts tend not to extend the aftertaste sensation as effectively. For example, as seen in FIGS. 1-7, use of pectin in the range of about 0.2% to about 0.4% by weight, particularly about 0.3% by weight, extends the aftertaste sensation for at least one to three minutes after the confectionery composition is substantially consumed.

Figure 1:
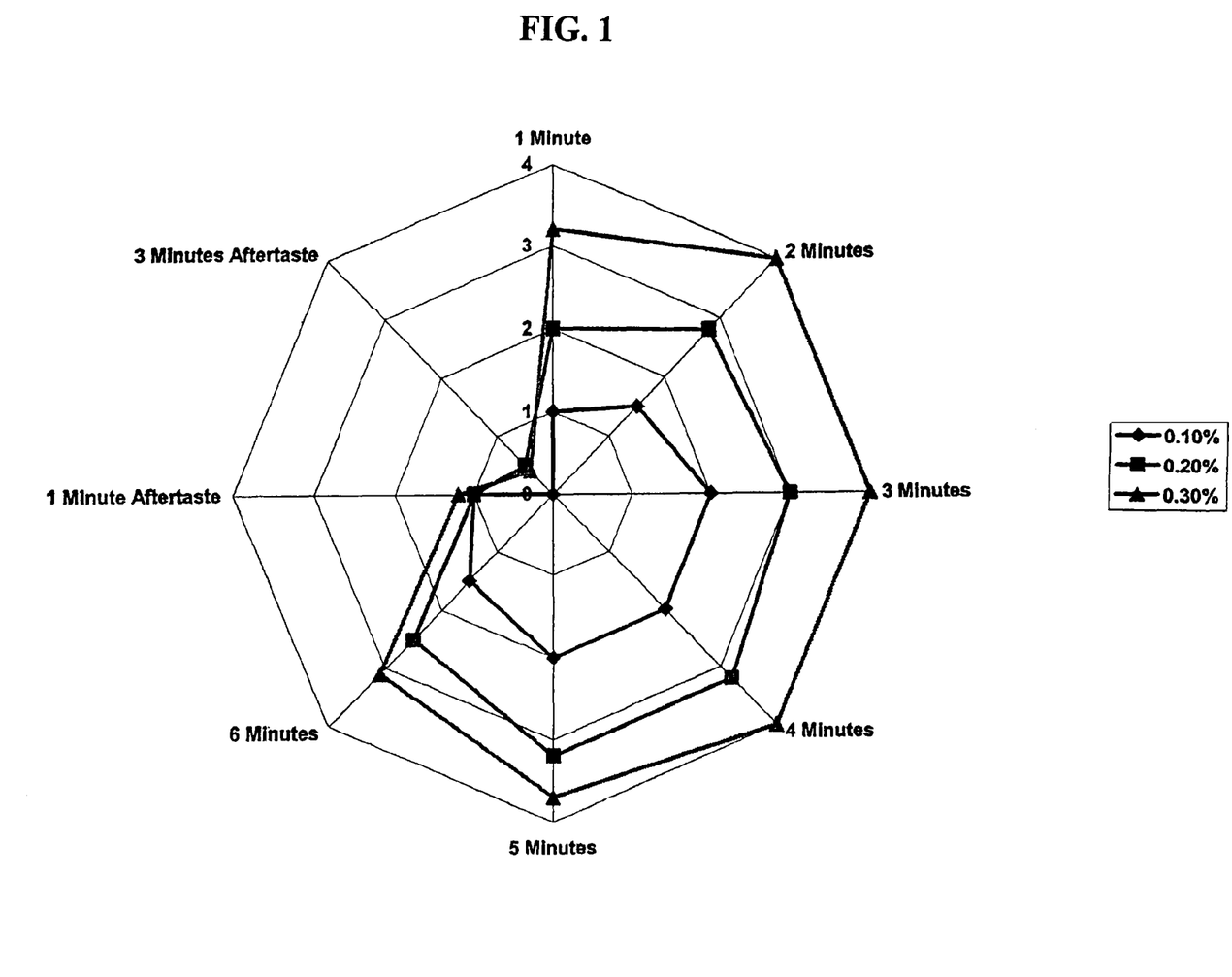
FIG. 1 is a graphical representation of the mouth and tongue warming intensity of lozenges containing various amounts of pectin.
Figure 2:
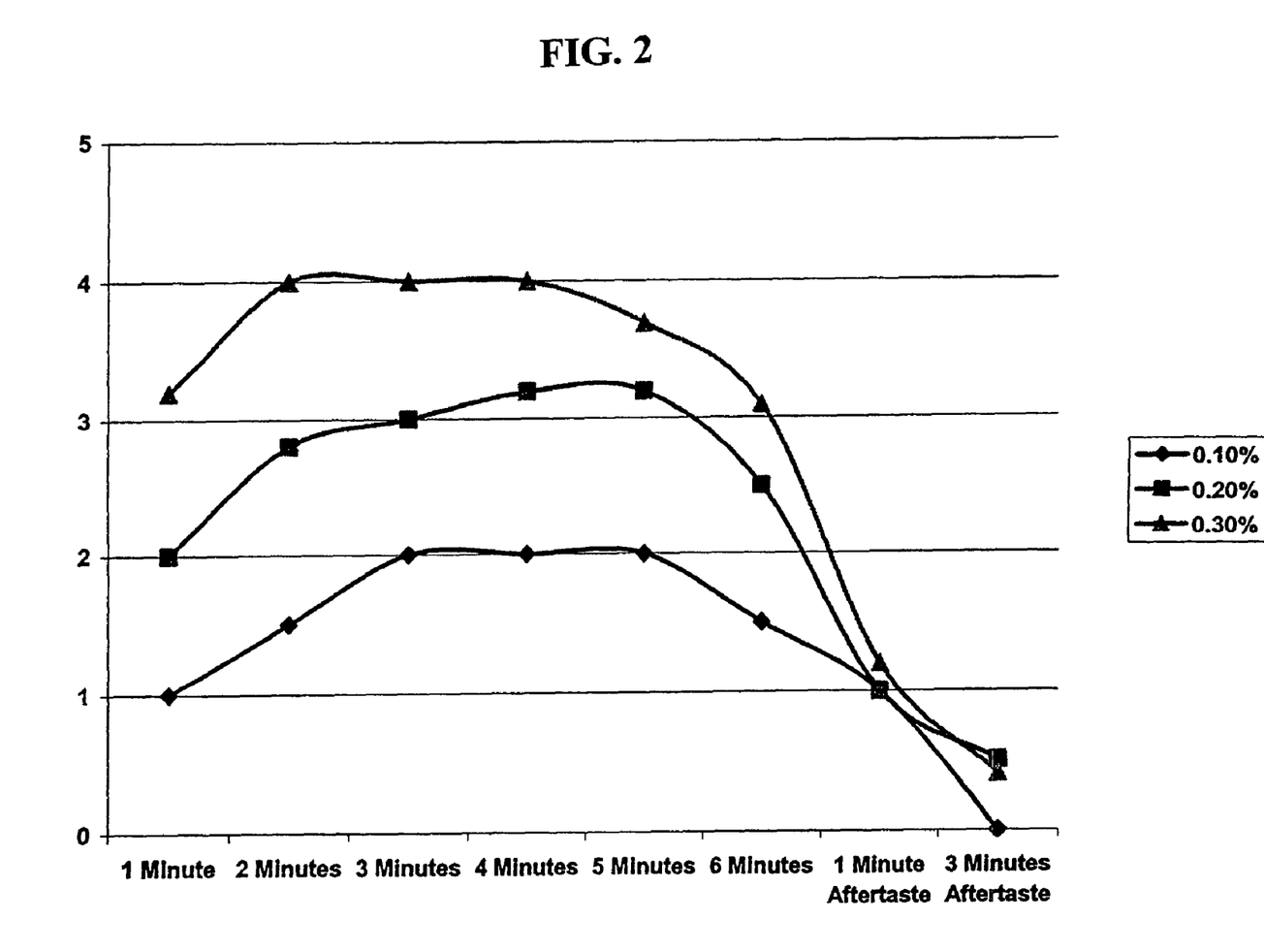
FIG. 2 is another graphical representation of the mouth and tongue warming intensity of the lozenges of FIG. 1.
Figure 3:
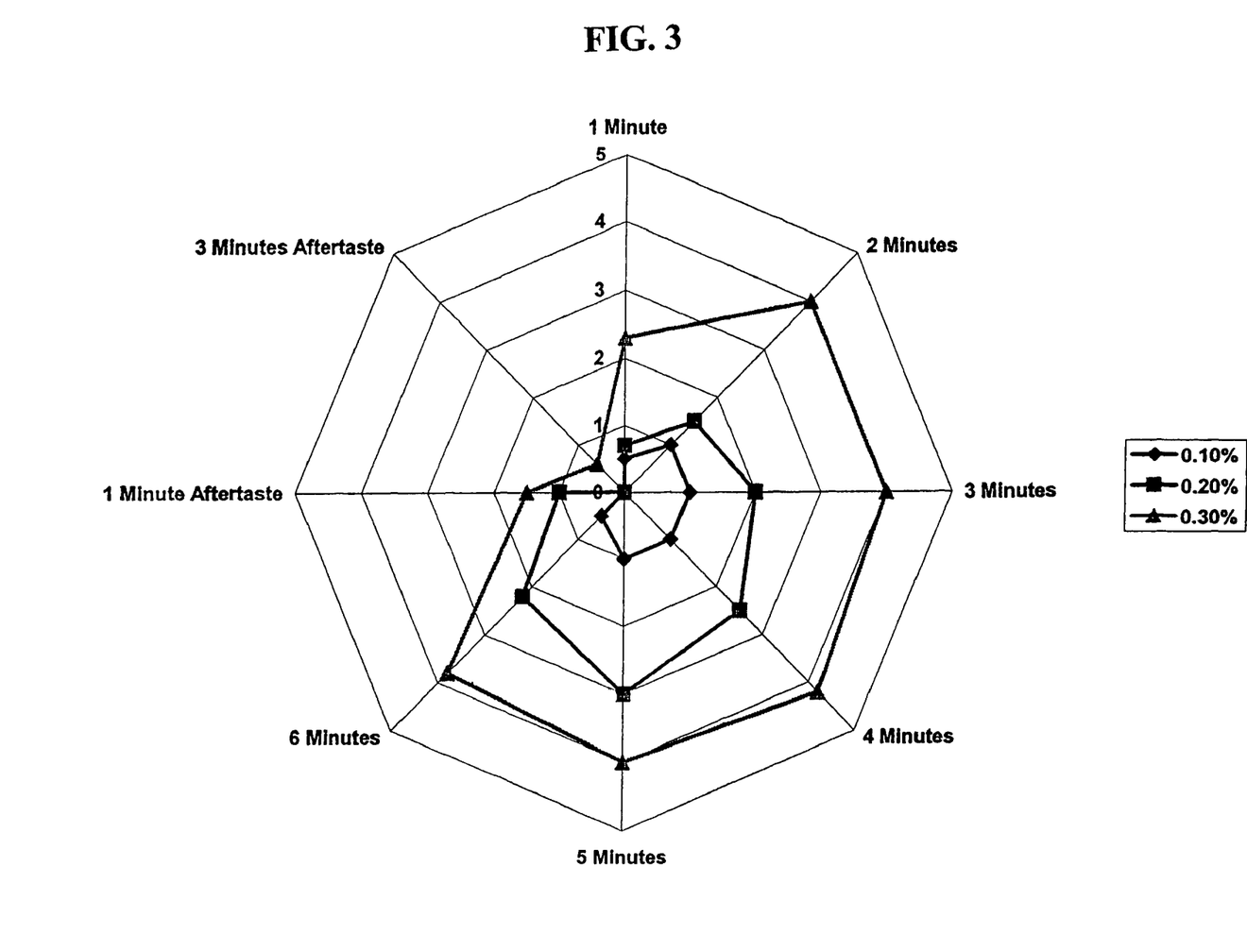
FIG. 3 is a graphical representation of the throat warming intensity of the lozenges of FIG. 1.
Figure 4:
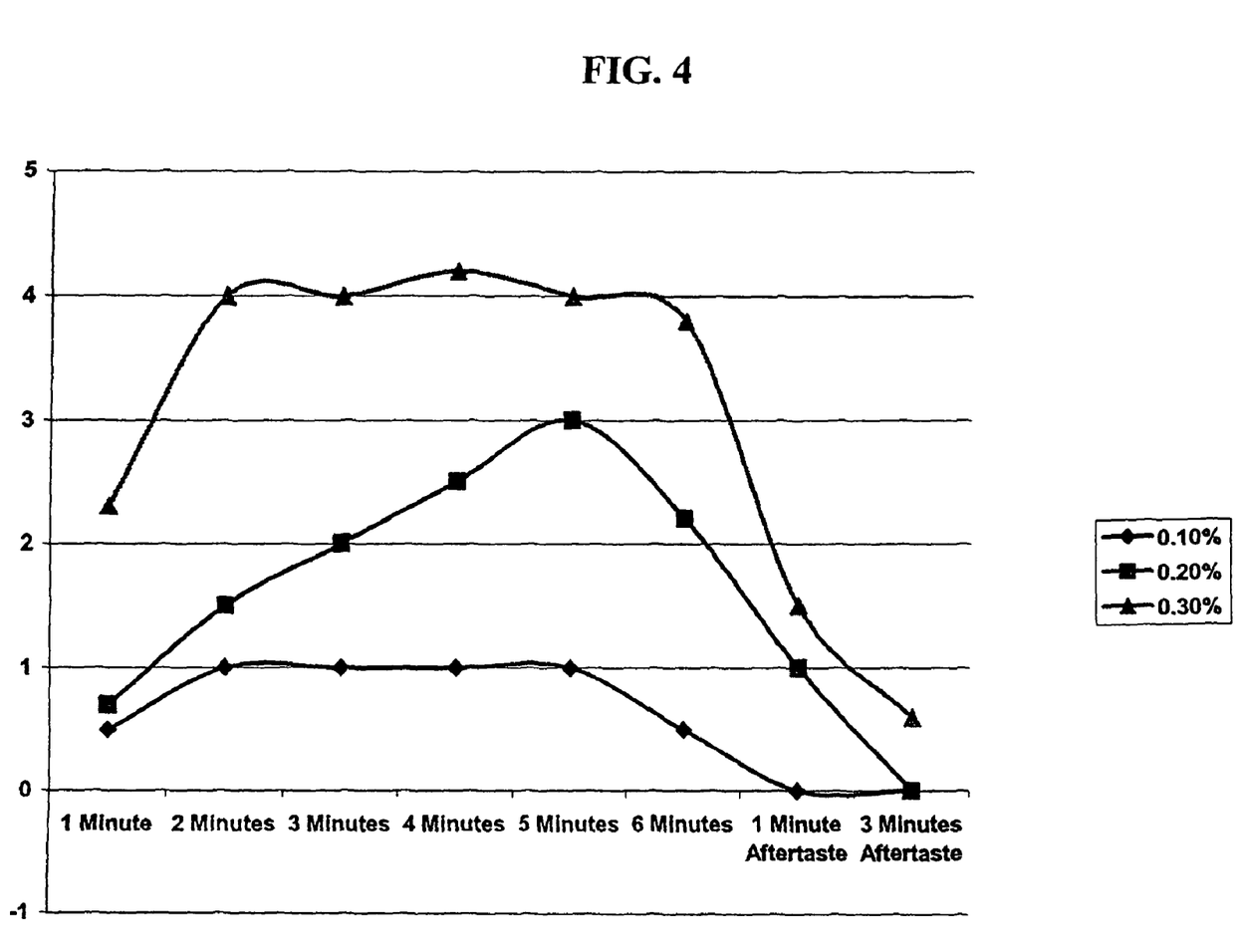
FIG. 4 is another graphical representation of the throat warming intensity of the lozenges of FIG. 1.

In particular, FIGS. 1 and 2 display the intensity of warming sensation felt in the mouth of the user upon consuming lozenges of the present invention incorporating a warming agent as the sensate and various levels of pectin (about 0.1%, 0.2% and 0.3% by weight), whereas FIGS. 3 and 4 show the intensity felt in the throat. As seen in these figures, about 0.2% and about 0.3% pectin by weight effectively extend the warming sensation in the mouth and throat throughout the six minutes of consumption, as well as about one to three minutes thereafter. Although pectin levels of about 0.1% by weight extend the warming sensation throughout consumption, the aftertaste is limited in duration as compared to the higher levels of pectin.

Figure 5:
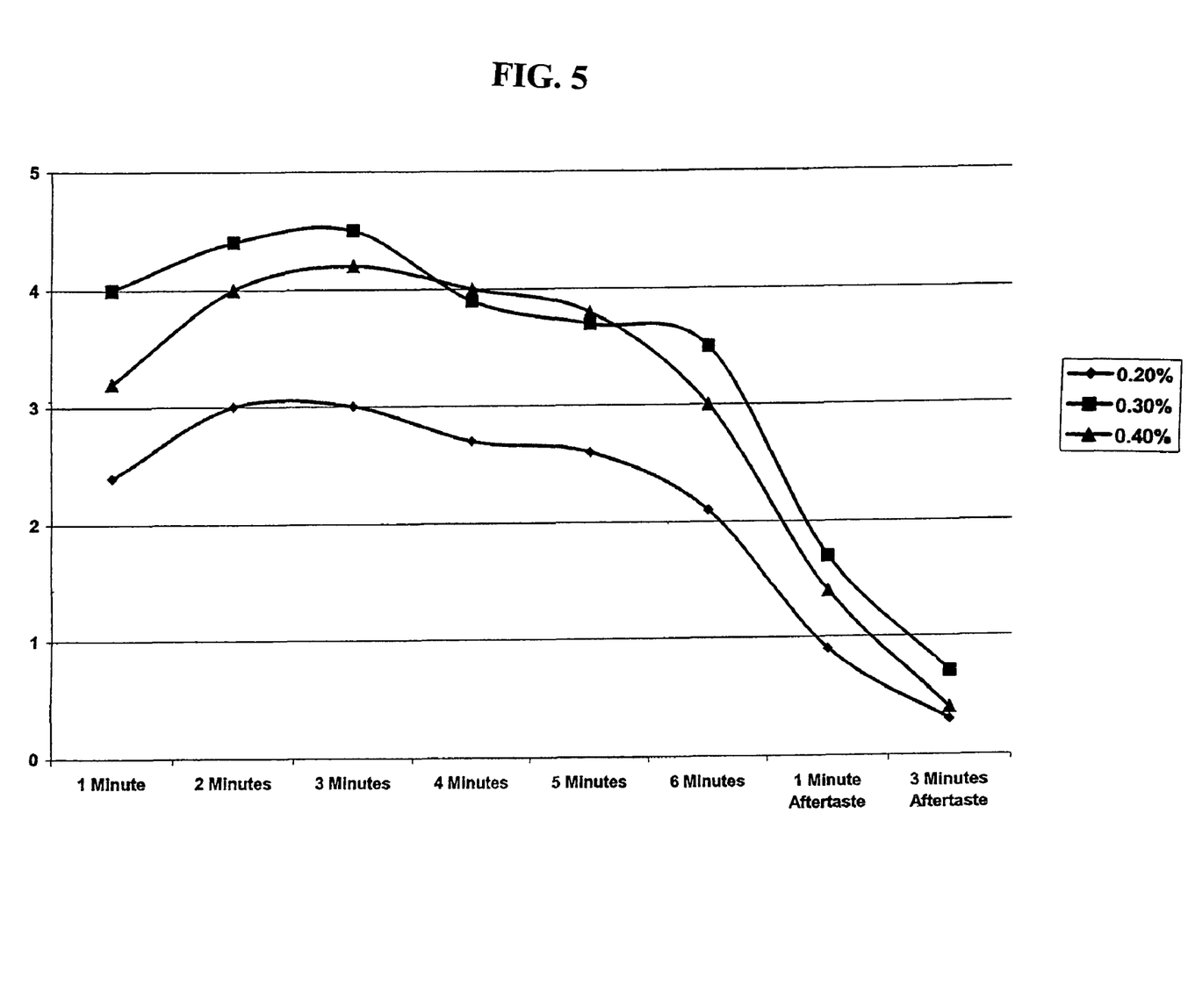
FIG. 5 is a graphical representation of the mouth and tongue warming intensity of lozenges containing various amounts of pectin.
Figure 6:
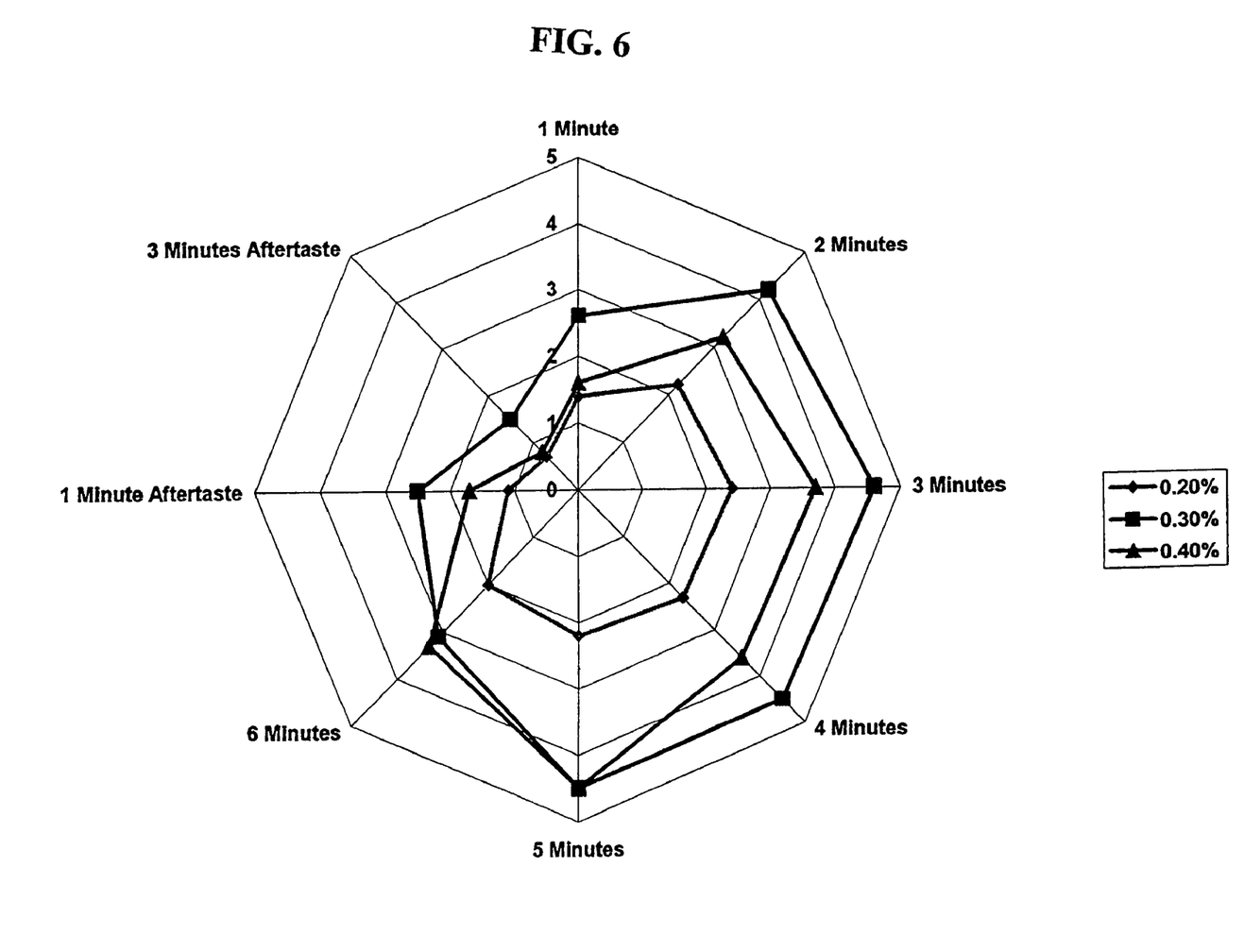
FIG. 6 is a graphical representation of the throat warming intensity of the lozenges of FIG. 5.
Figure 7:
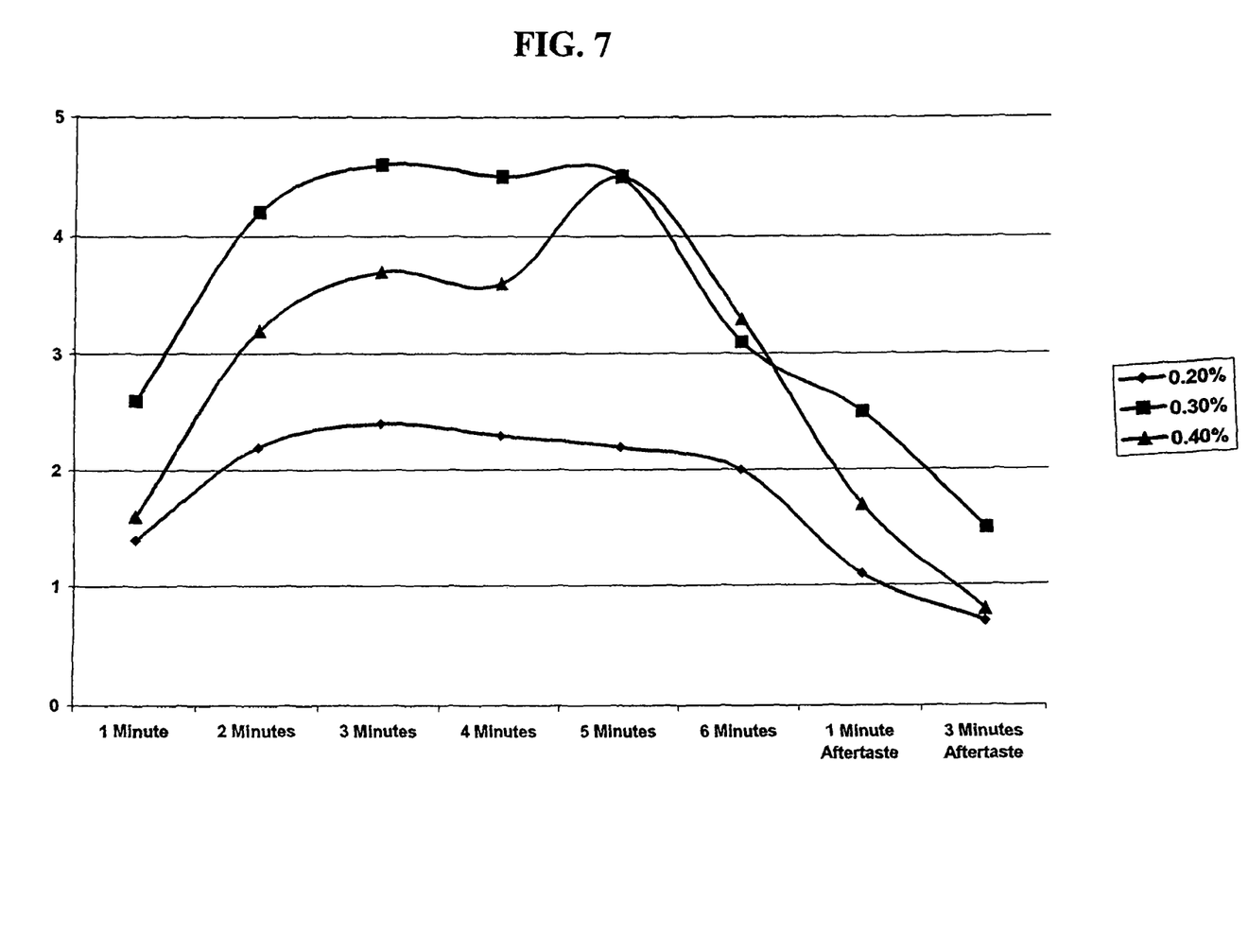
FIG. 7 is another graphical representation of the throat warming intensity of the lozenges of FIG. 5.

FIGS. 5-7 display the intensity of warming sensation of different amounts of pectin (about 0.2%, 0.3% and 0.4% by weight). FIG. 5 displays the intensity perceived in the mouth, whereas FIGS. 6 and 7 show the intensity in the throat, each at the varying levels of pectin. These figures show that about 0.2%, 0.3% and 0.4% by weight pectin effectively extend the warming sensation in the mouth and throat throughout the six minutes of consumption, as well as about one to three minutes thereafter. Even higher levels of pectin may be used. Therefore, ranges of about 0.2% to about 0.4% by weight establish a balance between properties, providing control of release without burning irritation.

In some embodiments, particularly lozenges or hard candies, the sensate, which is dispersed in a glassy polymer matrix, may be present in the composition in amounts of about 0.001% to about 10% by weight of the composition, more desirably about 0.001% to about 5% by weight. Amounts greater than about 5% by weight may cause a burning sensation or irritation to the user, unless ameliorated by other components.

The present invention also is directed to methods of preparing confectionery compositions. Such confections may be prepared using conventional apparatus such as fire cookers, cooking extruders, and/or vacuum cookers.

In accordance with the present invention, the carrier (e.g., bulk sweetener) and a solvent (e.g., water), are combined in a mixing vessel to form a slurry. The slurry is heated to about 70° C. to 120° C. to dissolve any sweetener crystals or particles and form an aqueous solution. Once dissolved, heat and optionally vacuum are applied to cook the batch and boil off water until a residual moisture of less than about 4% is achieved. For example, batch cookers may be employed. The batch changes from a crystalline to an amorphous, or glassy, phase. The sensate composition and flavor agents are then admixed in the batch by mechanical mixing operations, along with any other optional additives, such as coloring agents. The batch is then cooled to about 50° C. to 10° C. to attain a semi-solid or plastic-like consistency.

The optimum mixing required to uniformly mix the sensate compositions, flavors, colorants and other additives into the batch during manufacturing of hard confectionery is determined by the time needed to obtain a uniform distribution of the materials. Normally, mixing times of from one to ten minutes have been found to be acceptable.

Once the candy mass has been properly tempered, it may be cut into workable portions or formed into desired shapes having the correct weight and dimensions. A variety of forming techniques may be utilized depending upon the shape and size of the final product desired. Once the desired shapes are formed, cool air is applied to allow the comestibles to set uniformly, after which they are wrapped and packaged.

The apparatus useful in accordance with the present invention comprises cooking and mixing apparatus well known in the confectionery manufacturing arts, and selection of the specific apparatus will be apparent to one skilled in the art.

Some other embodiments of the present invention include chewing gum compositions. The carrier in chewing gum compositions may include a gum base and other optional components. The gum base may include any component known in the chewing gum art. For example, the gum base may include elastomers, bulking agents, waxes, elastomer solvents, emulsifiers, plasticizers, fillers and mixtures thereof.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight, desirably from about 35% to about 40% by weight.

In some embodiments, the gum base may include wax. It softens the polymeric elastomer mixture and improves the elasticity of the gum base. When present, the waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include hydrogenated vegetable oils, such as soybean oil and cottonseed oils, which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

In some embodiments, the gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional ingredients may be optionally included in the gum base in effective amounts such as flavor agents and coloring agents described above, antioxidants, preservatives, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, vitamin E and mixtures thereof, may also be included. Other conventional chewing gum additives known to one having ordinary skill in the chewing gum art may also be used in the gum base.

The chewing gum compositions may include amounts of conventional additives selected from the group consisting of sweetening agents, plasticizers, softeners, emulsifiers, waxes, fillers, bulking agents (carriers, extenders, bulk sweeteners), mineral adjuvants, flavor agents and coloring agents discussed above, antioxidants, acidulants, thickeners, medicaments, and the like, and mixtures thereof. Some of these additives may serve more than one purpose. For example, in sugarless gum compositions, a sweetener, such as maltitol or other sugar alcohol, may also function as a bulking agent.

Bulk sweeteners, as described above, generally are present in amounts of about 5% to about 95% by weight of the chewing gum composition.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants.

Other conventional gum additives known to one having ordinary skill in the chewing gum art also may be used in the chewing gum compositions.

The sensates may be present in the chewing gum compositions in amounts of about 0.001% to about 10% by weight of the composition. In particular, it may be desirable to use higher amounts of sensates in chewing gums, i.e., upwards of about 10%, as compared to lozenges, hard candy and the like, as less than all of the sensate is released from the gum during chew. To achieve a sufficient sensation, therefore, higher amounts may be incorporated therein. In addition, the desired sensation will last longer in chewing gums due to the length of chew time, i.e., up to about one hour.

Methods of making chewing gum are not discussed in detail herein as they are well known to one having ordinary skill in the chewing gum art. For general chewing gum preparation processes see U.S. Pat. No. 4,271,197 to Hopkins et al, U.S. Pat. No. 4,352,822 to Cherukuri et al and U.S. Pat. No. 4,497,832 to Cherukuri et al, each of which is incorporated herein by reference in its entirety.

Methods of preparing other comestible products, including soft candy, cotton candy, pressed tablets, film, liquid and powdered beverages, and the like also are well known to those having ordinary skill in the art and need not be discussed in detail herein.

The features and advantages of the present invention are more fully shown by the following examples which are provided for purposes of illustration, and are not to be construed as limiting the invention in any way.

EXAMPLES

Example 1

TABLE 1

Tingling Sensate in hard-boiled candy

| Component | % by Weight |
| --- | --- |
| Candy base (Sucrose, glucose syrup 42De & water) | 98.60 |
| Citric Acid | 0.60 |
| Sensate (Tingling agent)[1] | 0.30 |
| Orange Flavor | 0.20 |
| Color solution | 0.30 |

[1]Proprietary component marketed under No. 596780 from Givaudan

A hard candy was prepared according to the formulation in Table 1 above.

The candy composition was prepared by dissolving the sugar/glucose syrup in water and cooking at 146° C. Color was added immediately to the cooked sugar mass. The batch was placed on a cooling table where flavor, tingling agent and acids were added. The batch was kneaded. Roll candies were dropped into the desired weight and size pieces.

Example 2

TABLE 2

Jambu Tingling Sensate in hard-boiled candy

| Component | % by Weight |
| --- | --- |
| Candy base (Sucrose, glucose syrup 42De & water) | 98.89 |
| Citric Acid | 0.60 |
| Sensate (Jambu tingling agent)[1] | 0.01 |
| Orange Flavor | 0.20 |
| Color solution | 0.30 |

[1]Proprietary component marketed under No. 030889 from Takasago

A hard candy was prepared according to the formulation in Table 2 above.

The candy composition was prepared by dissolving the sugar/glucose syrup in water and cooking at 146° C. Color was added immediately to the cooked sugar mass. The batch was placed on a cooling table where flavor, tingling agent and acids were added. The batch was kneaded. Roll candies were dropped into the desired weight and size pieces.

Example 3

TABLE 3

Jambu and Cooling Sensates in hard-boiled candy

| Component | % by Weight |
| --- | --- |
| Candy base (Sucrose, glucose syrup 42De & water) | 98.89 |
| Citric Acid | 0.60 |
| Sensate (Jambu tingling agent + cooling agent)[1] | 0.01 |
| Orange Flavor | 0.20 |
| Color solution | 0.30 |

[1]Proprietary component marketed under No. 030217 from Takasago

A hard candy was prepared according to the formulation in Table 3 above.

The candy composition was prepared by dissolving the sugar/glucose syrup in water and cooking at 146° C. Color was added immediately to the cooked sugar mass. The batch was placed on a cooling table where flavor, sensates and acids were added. The batch was kneaded. Roll candies were dropped into the desired weight and size pieces.

Example 4

TABLE 4

Succulence Sensate in hard-boiled candy

| Component | % by Weight |
| --- | --- |
| Candy base (Sucrose, glucose syrup 42De & water) | 98.70 |
| Citric Acid | 0.60 |
| Sensate (Succulence)[1] | 0.20 |
| Orange Flavor | 0.20 |
| Color solution | 0.30 |

[1]Proprietary component marketed under No. 032732 from International Flavors and Fragrances, Inc. (IFF)

A hard candy was prepared according to the formulation in Table 4 above.

The candy composition was prepared by dissolving the sugar/glucose syrup in water and cooking at 146° C. Color was added immediately to the cooked sugar mass. The batch was placed on a cooling table where flavor, sensate and acids were added. The batch was kneaded. Roll candies were dropped into the desired weight and size pieces.

Example 5

TABLE 5

Cool Tingling Sensate in hard-boiled candy

| Component | % by Weight |
| --- | --- |
| Candy base (Sucrose, glucose syrup 42De & water) | 98.75 |
| Citric Acid | 0.60 |
| Sensate (Cool Tingling Agent)[1] | 0.15 |
| Orange Flavor | 0.20 |
| Color solution | 0.30 |

[1]Proprietary component marketed under No. 362339 from IFF

A hard candy was prepared according to the formulation in Table 5 above.

The candy composition was prepared by dissolving the sugar/glucose syrup in water and cooking at 146° C. Color was added immediately to the cooked sugar mass. The batch was placed on a cooling table where flavor, cool tingling sensate and acids were added. The batch was kneaded. Roll candies were dropped into the desired weight and size pieces.

Example 6

TABLE 6

Tingling Sensate in hard-boiled candy (with pectin)

| Component | % by Weight |
| --- | --- |
| Candy base (Sucrose, glucose syrup 42De & water) | 84.95 |

TABLE 6-continued

Tingling Sensate in hard-boiled candy (with pectin)

| Component | % by Weight |
| --- | --- |
| Pectin solution (8% pectin powder, potassium citrate, water) | 13.75 |
| Citric Acid | 0.50 |
| Sensate (Tingling agent)[1] | 0.30 |
| Orange Flavor | 0.20 |
| Color solution | 0.30 |

[1]Proprietary component marketed under No. 596780 from Givaudan

A hard candy was prepared according to the formulation in Table 6 above.

Pectin and potassium citrates were dispersed in hot water (70° C.) with vigorous mixing to prepare the pectin solution. The candy composition was prepared by dissolving the sugar/glucose syrup in water and cooking at 146° C. The pectin solution and color were added to the cooked sugar mass. The batch was placed on a cooling table where flavor, tingling agent and acids were added. The batch was kneaded. Roll candies were dropped into the desired weight and size pieces.

Example 7

TABLE 7

Tingling Sensate in hard-boiled candy (with alginates)

| Component | % by Weight |
| --- | --- |
| Candy base (Sucrose, glucose syrup 42De & water) | 84.65 |
| Alginate solution in water (5%) | 13.75 |
| Citric Acid | 0.70 |
| Sensate (Tingling agent)[1] | 0.30 |
| Orange Flavor | 0.20 |
| Color solution | 0.40 |

[1]Proprietary component marketed under No. 596780 from Givaudan

A hard candy is prepared according to the formulation in Table 7 above.

Sodium alginate powder is dispersed in hot water (70° C.) with vigorous mixing. The candy composition is prepared by dissolving the sugar/glucose syrup in water and cooking at 146° C. The alginate solution and color are added to the cooked sugar mass. The batch is placed on a cooling table where flavor, tingling agent and acids are added. The batch is kneaded. Roll candies are dropped into the desired weight and size pieces.

Example 8

TABLE 8

Tingling Sensate in hard-boiled candy (with carboxymethyl cellulose (CMC))

| Component | % by weight |
| --- | --- |
| Candy Base (sugar, glucose syrup 42DE and water) | 83.70 |
| Color solution | 0.40 |
| CMC solution in water (0.025% water) | 15.21 |
| Flavor | 0.17 |
| Tingling sensate[1] | 0.52 |

[1]Proprietary component marketed under No. 596780 from Givaudan

A hard candy is prepared according to the formulation in Table 8 above.

CMC is dispersed in hot water (70° C.) and mixed using a high shear mixer. The candy composition is prepared by dissolving the sugar/glucose syrup in water and cooking at 146° C. The CMC solution and color are added to the cooked sugar mass. The batch is placed on a cooling table where flavor and tingling sensate are added. The batch is kneaded. Roll candies are dropped into the desired weight and size pieces.

Example 9

TABLE 9

Tingling Sensates in Soft/Chewy Candy

| Component | % by weight |
|---|---|
| Sugar, corn syrup and water | 84.98 |
| Sensate (Tingling agent)[1] | 0.40 |
| Gel base (gelatin +/− pectin) and water | 5.00 |
| Citric acid | 0.10 |
| Malic acid | 0.20 |
| Color solution | 0.11 |
| Flavor | 0.25 |
| Fat | 8.25 |
| Pulverized sugar | 0.71 |

[1]Proprietary component marketed under No. 596780 from Givaudan

A soft, chewy candy is prepared according to the formulation in Table 9 above.

The candy composition is prepared by first forming the gel base by adding gelatin, with or without pectin, to warm water and then mixing. The gel base is then combined with the citric and malic acids and color solution and mixed in a Hobart mixer.

The sugar and corn syrup mixture is heated to about 130° C. and added to the gel base and other components in the Hobart mixer. The combination is mixed at speed three for thirty seconds and then mixed at speed two for five minutes.

The fat is heated until it is melted and then combined with the flavor and sensate to form a premix. The Hobart mixer speed then is reduced to one and the melted fat, flavor and sensate premix is added thereto.

The mixer speed is changed to three for thirty seconds, then speed two for three minutes, and then speed one at which point the pulverized sugar is added. The batch is again mixed for two minutes and then poured onto a cooling table. The batch is folded until cool, sampled and hand-pulled for one and a half minutes. The batch is poured into molds and subsequently grained and cut into the desired weight and size pieces.

Example 10

TABLE 10

Tingling Sensates in Breath Film

| Component | % by weight (wet basis) |
|---|---|
| Sweetener blend (xylitol, Ace-sulfame K, sucralose) | 2.82 |
| Water | 66.32 |
| Color solution (FD&C Yellow #6) | 2.00 |
| Hydrocolloid blend (sodium alginate, pectin, modified starch) | 17.47 |

TABLE 10-continued

Tingling Sensates in Breath Film

| Component | % by weight (wet basis) |
|---|---|
| Flavor | 7.76 |
| Sensate (Tingling agent[1] + cooling agent[2]) | 0.40 |
| Plasticizer (glycerin) | 3.23 |

[1]Proprietary component marketed under No. 596780 from Givaudan
[2]Proprietary component marketed as "Cooler 2" from IFF A breath film is prepared according to the fonnulation in Table 10 above.

The film is prepared by first dissolving the sweeteners (xylitol, Ace-sulfame K and sucralose) and color in water. The hydrocolloids are added and dispersed in the solution. A high shear mixer is used, as necessary, to remove lumps. The hydrocolloids are allowed to hydrate for one and a half hours, after which the plasticizer (glycerine), sensates and flavor are added. The batch is mixed and allowed to rest for fifteen to thirty minutes.

Subsequently, the film is cast on a hot plate at 74° C. In particular, a water bath is placed on the hot plate, and the film is cast onto a stainless steel plate that is placed above the water bath. If the temperature of the hot plate becomes too high, i.e., boiling water, the film fuses to the plate causing difficulties in removal. Once dried, the film is peeled from the plate and after equilibration (about twenty-four hours) strips are cut.

Example 11

TABLE 11

Tingling Sensates in Beverages

| Component | Weight in g |
|---|---|
| High fructose corn syrup-55 (77 deg Brix) | 160.00 |
| Citric acid, anhydrous | 2.50 |
| Tingling agent[1] | 0.50 |
| Water | 837.00 |

[1]Proprietary component marketed under No. 596780 from Givaudan

A liquid beverage may be prepared according to the formulation in Table 11 above. The beverage composition is prepared by combining the above-listed ingredients, stirring to mix and pasteurizing at about 190° F. for about two minutes.

The invention claimed is:

1. A lozenge composition comprising:
an amorphous glassy polymer matrix comprising pectin present in an amount of about 0.2% to about 0.4% by weight of said composition and having a tingling sensate dispersed therein; wherein the tingling sensate is selected from the group consisting of Jambu Oleoresin, Japanese pepper extract, black pepper extract, Echinacea extract, Northern Prickly Ash extract, red pepper oleoresin, effervescing agents, and combinations thereof; and
wherein said amount of pectin is sufficient to extend an aftertaste sensation of said sensate for about one to three minutes after said composition is consumed.

2. The lozenge composition according to claim 1, wherein said glassy polymer matrix comprises a hydrated food-grade polymer present in an amount sufficient to produce a sensation in the mouth and upper gastrointestinal tract of a mammal extending from about 2 seconds to about 30 minutes.

3. The lozenge composition according to claim 2, wherein said tingling sensate is present in an amount of about 0.001% to about 5% by weight of said composition.

4. An amorphous glassy polymer matrix comprising:
a candy base and a non-particulate matrix comprising pectin and a dispersion of tingling sensate therein; wherein the tingling sensate is selected from the group consisting of Jambu Oleoresin, Japanese pepper extract, black pepper extract, Echinacea extract, Northern Prickly Ash extract, red pepper oleoresin, effervescing agents, and combinations thereof; wherein the dispersion allows potential chemical and physical interactions between said pectin and said tingling sensate, wherein said pectin is present in an amount of about 0.2% to about 0.4% by weight of the total composition and wherein said amount of pectin is sufficient to extend an aftertaste sensation of said tingling sensate for about one to three minutes after said composition is consumed.

5. An amorphous glassy polymer matrix comprising:
a tingling sensate in an amount of about 0.005 to about 10% weight percent; wherein the tingling sensate is selected from the group consisting of Jambu Oleoresin, Japanese pepper extract, black pepper extract, Echinacea extract, Northern Prickly Ash extract, red pepper oleoresin, effervescing agents, and combinations thereof; and
a hydrated food grade polymer comprising pectin in an amount of about 0.2 to about 0.4% weight percent,
wherein said tingling sensate and said pectin are dispersed throughout a candy base such that upon consumption of said amorphous glassy polymer matrix, said pectin and said tingling sensate interact chemically and/or physically to permit controlled release of tingling sensate from the amorphous glassy polymer matrix
wherein said amount of pectin is sufficient to extend an aftertaste sensation of said tingling sensate for about one to three minutes after said amorphous glassy polymer matrix is consumed.

6. The amorphous glassy polymer matrix claim 5, further comprising a flavor in an amount of about 0.2 to about 5% weight percent.

7. The lozenge composition according to claim 1, wherein the pectin is hydrated.

8. The amorphous glassy polymer matrix of claim 4, wherein the pectin is hydrated.

9. The amorphous glassy polymer matrix of claim 5, wherein the pectin is hydrated.

10. The lozenge composition of claim 1 comprising pectin present in an amount of 0.1% to 0.3% by weight of said composition.

11. The amorphous glassy polymer matrix of claim 4, comprising pectin present in an amount of 0.1% to 0.3% by weight of said glassy polymer matrix.

12. The amorphous glassy polymer matrix of claim 5 comprising pectin present in an amount of 0.1% to 0.3% by weight of said glassy polymer matrix.

\* \* \* \* \*